(12) United States Patent
Chau et al.

(10) Patent No.: US 6,626,850 B1
(45) Date of Patent: Sep. 30, 2003

(54) AUTOMATED BIOPSY INSTRUMENTS

(75) Inventors: Sonny Chau, Gurnee, IL (US); Jan Como-Rodriguez, Libertyville, IL (US); Thomas Kupec, Gurnee, IL (US)

(73) Assignee: Allegiance Corporation, McGaw Park, IL (US)

( * ) Notice: Subject to any disclaimer, the term of this patent is extended or adjusted under 35 U.S.C. 154(b) by 0 days.

(21) Appl. No.: 09/050,786

(22) Filed: Mar. 30, 1998

Related U.S. Application Data

(62) Division of application No. 08/474,756, filed on Jun. 7, 1995, now Pat. No. 5,779,647.

(51) Int. Cl.⁷ ............................................. A61B 10/00
(52) U.S. Cl. ..................................................... 600/567
(58) Field of Search ................................. 600/564, 567, 600/566, 568, 167, 170

(56) References Cited

U.S. PATENT DOCUMENTS

| 387,761 A | 8/1888 | Briggs |
| 845,792 A | 3/1907 | Jenkins |
| 1,246,258 A | 11/1917 | Gerace |

(List continued on next page.)

FOREIGN PATENT DOCUMENTS

| CH | 483829 | 1/1970 |
| DE | 141108 | 2/1901 |
| DE | 3909575 C1 | 8/1990 |
| EP | 029 864 A1 | 12/1979 |
| EP | 0 010 321 A1 | 4/1980 |
| EP | 066 465 A2 | 12/1982 |
| EP | 153 047 A2 | 8/1985 |
| EP | 173 653 A2 | 3/1986 |
| EP | 0 207 726 A2 | 6/1986 |
| EP | 186 256 A1 | 7/1986 |
| EP | 317 503 A2 | 11/1988 |
| EP | 318 447 A1 | 5/1989 |
| GB | 683814 | 6/1950 |
| GB | 1255330 | 12/1971 |
| GB | 2177307 A | 1/1987 |
| RU | 175611 | 12/1965 |
| RU | 683726 | 9/1979 |
| RU | 1026794 A | 7/1983 |
| RU | 1551362 A1 | 3/1990 |
| RU | 1711848 A1 | 2/1992 |
| WO | WO 83/00112 | 1/1983 |
| WO | WO 83/03343 | 10/1983 |
| WO | WO 87/06815 | 11/1987 |
| WO | WO 88/07839 | 10/1988 |
| WO | WO 91/01112 | 2/1991 |
| WO | WO 91/01113 | 2/1991 |
| WO | WO 91/08707 | 6/1991 |
| WO | WO 91/16002 | 10/1991 |
| WO | WO 92/03096 | 3/1992 |
| WO | WO 93/22971 | 11/1993 |
| WO | WO 95/13752 | 5/1995 |
| WO | WO 96/04851 | 2/1996 |

OTHER PUBLICATIONS

Parker et al., "Image–Directed Percutaneous Biopsies with a Biopsy Gun," *Radiology*, pp. 663–669 (Jun. 1989).
Renzo, "A New Spring–Loaded Handle for Improved Needle Biopsy," *Br. J. Surg.*, 67:449–450 (1980).
Yellon, "A Multiple Biopsy Gun for the Study of Three–Dimentional Metabolic Geometry," *Physiological Society*, pp. 5P–6P (Apr. 1979).
"Tru Cut Disposable Biopsy Needle," Travenol Labratories, Inc., 2 pages (Oct. 1973).
"Biopty™ and Biopty–Cut™—Automatic System for Biopsies," Radiplast AB Sweeden, undated, 4 pages.

*Primary Examiner*—Max F. Hindenburg
*Assistant Examiner*—Pamela L Wingood
(74) *Attorney, Agent, or Firm*—Andrew G. Rozycki

(57) ABSTRACT

The present invention provides automated biopsy instruments especially useful for improving minimally invasive medical procedures to obtain soft tissue biopsy samples. The biopsy instruments provide side-by-side actuators which retract a stylet and a cannula in specific sequences. The biopsy instruments may include a single spring or two springs to sequentially fire the stylet and the cannula.

7 Claims, 8 Drawing Sheets

U.S. PATENT DOCUMENTS

| | | |
|---|---|---|
| 1,347,622 A | 7/1920 | Deininger |
| 1,434,388 A | 11/1922 | Hughes |
| 1,867,624 A | 7/1932 | Hoffman |
| 2,198,111 A | 4/1940 | Gorbatenko et al. |
| 2,426,535 A | 8/1947 | Turkel |
| 2,623,521 A | 12/1952 | Shaw |
| 2,632,949 A | 3/1953 | Falcone |
| 2,659,369 A | 11/1953 | Lipman |
| 2,689,562 A | 9/1954 | Adams et al. |
| 2,705,949 A | 4/1955 | Silverman |
| 2,818,852 A | 1/1958 | Kugler |
| 2,839,049 A | 6/1958 | MacLean |
| 2,850,007 A | 9/1958 | Lingley |
| 2,923,295 A | 2/1960 | Guerriero |
| 2,945,316 A | 7/1960 | Mulno |
| 3,030,959 A | 4/1962 | Grünert |
| 3,175,554 A | 3/1965 | Stewart |
| 3,215,264 A | 11/1965 | Silson et al. |
| 3,274,976 A | 9/1966 | Levoin |
| 3,477,423 A | 11/1969 | Griffith |
| 3,487,834 A | 1/1970 | Smith, Jr. et al. |
| 3,506,007 A | 4/1970 | Henkin |
| 3,561,429 A | 2/1971 | Jewett |
| 3,592,192 A | 7/1971 | Harautuneian |
| 3,595,217 A | 7/1971 | Rheinfrank |
| 3,692,020 A | 9/1972 | Schied |
| 3,762,416 A | 10/1973 | Moss et al. |
| 3,835,860 A | 9/1974 | Garretson |
| 3,879,847 A | 4/1975 | Roll |
| 3,905,365 A | 9/1975 | Colombo |
| 3,989,033 A | 11/1976 | Halpern et al. |
| 3,995,619 A | 12/1976 | Glatzer |
| 4,013,080 A | 3/1977 | Froning |
| 4,022,535 A | 5/1977 | Ritter |
| 4,073,321 A | 2/1978 | Moskowitz |
| 4,099,518 A | 7/1978 | Baylis et al. |
| 4,142,517 A | 3/1979 | Stavropoulos et al. |
| 4,169,475 A | 10/1979 | Genese |
| 4,177,797 A | 12/1979 | Baylis et al. |
| 4,178,810 A | 12/1979 | Takahashi |
| 4,230,123 A | 10/1980 | Hawkins, Jr. |
| 4,254,762 A | 3/1981 | Yoon |
| 4,256,119 A | 3/1981 | Gauthier |
| 4,266,555 A | 5/1981 | Jamshidi |
| 4,275,728 A | 6/1981 | Merry |
| 4,282,884 A | 8/1981 | Boebel |
| 4,308,859 A | 1/1982 | Child |
| 4,308,875 A | 1/1982 | Young |
| 4,333,457 A | 6/1982 | Margulies |
| 4,345,589 A | 8/1982 | Hiltebrandt |
| 4,356,828 A | 11/1982 | Jamshidi |
| 4,362,156 A | 12/1982 | Feller, Jr. et al. |
| 4,379,458 A | 4/1983 | Bauer et al. |
| 4,396,021 A | 8/1983 | Baumgartner |
| 4,402,324 A | 9/1983 | Lindgren et al. |
| 4,411,654 A | 10/1983 | Boarini et al. |
| 4,416,278 A | 11/1983 | Miller |
| 4,445,893 A | 5/1984 | Bodicky |
| 4,461,305 A | 7/1984 | Cibley |
| 4,476,864 A | 10/1984 | Tezel |
| 4,488,545 A | 12/1984 | Shen |
| 4,517,965 A | 5/1985 | Ellison |
| 4,525,157 A | 6/1985 | Vaillancourt |
| 4,570,632 A | 2/1986 | Woods |
| 4,592,745 A | 6/1986 | Rex et al. |
| 4,594,073 A | 6/1986 | Stine |
| 4,600,014 A | 7/1986 | Beraha |
| 4,601,710 A | 7/1986 | Moll |
| 4,605,011 A | 8/1986 | Näslund |
| 4,609,370 A | 9/1986 | Morrison |
| 4,617,940 A | 10/1986 | Wang |
| 4,619,272 A | 10/1986 | Zambelli |
| 4,620,547 A | 11/1986 | Boebel |
| 4,651,752 A | 3/1987 | Fuerst |
| 4,655,226 A | 4/1987 | Lee |
| 4,660,570 A | 4/1987 | Dombrowski |
| 4,667,684 A | 5/1987 | Leigh |
| 4,685,904 A | 8/1987 | Kres |
| 4,699,154 A | 10/1987 | Lindgren |
| 4,702,261 A | 10/1987 | Cornell et al. |
| 4,713,057 A | 12/1987 | Huttner et al. |
| 4,723,545 A | 2/1988 | Nixon et al. |
| 4,733,671 A | 3/1988 | Mehl |
| 4,735,215 A | 4/1988 | Goto et al. |
| 4,738,664 A | 4/1988 | Pringle |
| 4,747,414 A | 5/1988 | Brossel |
| 4,747,831 A | 5/1988 | Kulli |
| 4,758,233 A | 7/1988 | Phillips et al. |
| 4,762,516 A | 8/1988 | Luther et al. |
| 4,766,906 A | 8/1988 | Wang |
| 4,766,907 A | 8/1988 | de Groot et al. |
| 4,776,346 A | 10/1988 | Beraha et al. |
| 4,790,329 A | 12/1988 | Simon |
| 4,815,476 A | 3/1989 | Clossick |
| 4,834,717 A | 5/1989 | Haber et al. |
| 4,850,373 A | 7/1989 | Zatloukal et al. |
| D303,571 S | 9/1989 | Åkerfeldt |
| 4,881,551 A | 11/1989 | Taylor |
| 4,889,118 A | 12/1989 | Schwiegerling |
| 4,893,635 A | 1/1990 | de Groot et al. |
| 4,895,147 A | 1/1990 | Bodicky et al. |
| D306,070 S | 2/1990 | Åkerfeldt |
| 4,903,709 A | 2/1990 | Skinner |
| 4,907,599 A | 3/1990 | Taylor |
| 4,917,100 A | 4/1990 | Nottke |
| 4,919,146 A | 4/1990 | Rhinehart et al. |
| 4,924,878 A | 5/1990 | Nottke |
| D309,014 S | 7/1990 | Åkerfeldt |
| 4,944,308 A | 7/1990 | Åkerfeldt |
| 4,950,265 A | 8/1990 | Taylor |
| 4,953,558 A | 9/1990 | Akerfeldt |
| 4,958,625 A | 9/1990 | Bates et al. |
| 4,976,269 A | 12/1990 | Mehl |
| 4,986,278 A | 1/1991 | Ravid et al. |
| 5,036,860 A | 8/1991 | Leigh et al. |
| 5,048,991 A | 9/1991 | Guo |
| 5,090,419 A | 2/1992 | Palestrant |
| 5,092,870 A | 3/1992 | Mittermeier |
| 5,121,751 A | 6/1992 | Ranalletta |
| 5,125,413 A | 6/1992 | Baran |
| 5,133,359 A | 7/1992 | Kedem |
| RE34,056 E | 9/1992 | Lindgren et al. |
| 5,146,921 A | 9/1992 | Terwilliger et al. |
| 5,161,542 A | 11/1992 | Palestrant |
| 5,163,947 A | 11/1992 | Kvalo et al. |
| 5,183,052 A | 2/1993 | Terwilliger |
| 5,188,118 A | 2/1993 | Terwilliger |
| 5,195,533 A | 3/1993 | Chin et al. |
| 5,222,951 A | 6/1993 | Abidin et al. |
| 5,243,994 A | 9/1993 | Ranalletta |
| 5,257,632 A | 11/1993 | Turkel et al. |
| 5,284,156 A | 2/1994 | Schramm et al. |
| 5,368,045 A | 11/1994 | Clement et al. |
| 5,368,607 A | 11/1994 | Freitas |
| 5,374,252 A | 12/1994 | Banks et al. |
| 5,392,790 A | 2/1995 | Kanner et al. |

AUTOMATED BIOPSY INSTRUMENTS

RELATED APPLICATION DATA

This application is a divisional of parent U.S. patent application Ser. No. 08/474,756 filed Jun. 7, 1995, now U.S. Pat. No. 5,779,647 which issued on Jul. 14, 1998.

FIELD OF THE INVENTION

This invention generally relates to biopsy instruments. More specifically, this invention relates to automated biopsy instruments especially useful for improving minimally invasive medical procedures to obtain soft tissue biopsy samples.

BACKGROUND OF THE INVENTION

A soft tissue biopsy procedure is a medical procedure for removing a soft tissue sample from a human or animal. The tissue sample can be analyzed to assist a medical professional in formulating a diagnosis. The biopsy procedure is a minimally invasive procedure for obtaining the tissue sample.

The biopsy procedure can be performed utilizing various techniques and devices. Typically, a biopsy device includes an inner stylet slidably positioned inside an outer cannula. The stylet is a solid, pointed needle having a tissue sampling recess, and the cannula is a hollow, open ended needle having a sharp tip. The stylet and the cannula are manipulated to capture a tissue sample in the sample recess. Existing biopsy devices include manual, semi-automated, and automated devices.

Manual biopsy devices allow for manual movement of the stylet and the cannula. Initially, the stylet and the cannula are inserted into soft tissue with the cannula covering the stylet tissue recess. Next, the stylet is manually advanced into the soft tissue to expose the tissue recess and to allow tissue to prolapse into the recess. The cannula is then manually advanced to sever the tissue and capture a tissue sample within the recess. Next, the stylet or the entire the biopsy device is withdrawn from the patient and the tissue sample removed from the recess.

Existing manual biopsy devices have exhibited drawbacks. For example, manual devices require the use of two hands to advance the stylet while holding the cannula in position, and to hold the stylet in position while advancing the cannula. This biopsy technique requires great manual dexterity and coordination. Further, the cutting speed of the manually advanced cannula is quite slow which may result in a poor quality tissue sample.

Existing semi-automatic biopsy devices provide stylet and cannula advancement motions similar to manually operated devices. After the stylet is manually advanced, the semi-automatic devices typically include a compression spring that advances the cannula to capture a tissue sample. The semi-automatic devices still require manual manipulation of the stylet.

Existing automatic biopsy devices also provide stylet and cannula advancement motions to capture a tissue sample in a stylet sample recess. The automatic devices generally include two compression springs to advance the stylet and the cannula. A first compression spring advances the stylet forward after a firing button is depressed. A second compression spring subsequently advances the cannula forward to sever and capture a tissue sample. Existing automatic devices have exhibited drawbacks. For example, automatic devices have required the use of two hands to cock the device (compress the springs). One device purports to be cockable with a single hand; but, the hand must change positions after cocking the cannula in order to cock the stylet. Changing hand positions is cumbersome and encourages two handed cocking. Additionally, as a compression spring expands, the spring force decreases. As the spring force decreases, the stylet and cannula speeds decrease, which may compromise the quality of the tissue sample. Also, existing automatic devices have provided insufficient time to allow the tissue to relax into the sample recess. Consequently, the size of the tissue sample may be reduced.

Existing biopsy devices have been designed to be either reusable or disposable. The reusable devices include a reusable handle and disposable needle assemblies. The stylet and cannula are removable from the handle and disposable with a new stylet and cannula. The handle can be cleaned and re-sterilized after use and thus, is reusable. Disposable devices include a permanent stylet and cannula and are not re-sterilizable. Accordingly, disposable devices are used on a single patient and then discarded.

Examples of existing biopsy devices are disclosed in U.S. Pat. Nos. 4,600,014; 4,944,308; 4,958,625; 5,368,045; and Re34,056. A reusable automatic device containing a single spring for stylet and cannula advancement is disclosed in U.S. Pat. No. 5,121,751.

Therefore, needs exist to improve biopsy devices. Particularly, needs exist to improve automated biopsy instruments especially useful for minimally invasive medical procedures to obtain soft tissue biopsy samples. The present invention satisfies these and other needs to improve biopsy devices.

Other aspects and advantages of the present invention will become apparent after reading this disclosure, including the claims, and reviewing the accompanying drawings.

SUMMARY OF THE INVENTION

The present invention provides automated biopsy instruments especially useful for improving minimum invasive medical procedures to obtain soft tissue biopsy samples. The biopsy instruments provide side-by-side actuators which retract a stylet and a cannula in specific sequences. The retraction sequences include cannula retraction with subsequent stylet retraction, and simultaneous cannula and stylet retraction. The side-by-side design of the cannula and stylet actuators allow the biopsy instrument to be operated with a single human hand without repositioning the hand The biopsy instruments may include a single spring or two springs to sequentially fire the stylet and the cannula. A constant force spring is utilized in the single spring embodiment. The single spring embodiment also includes an engagement mechanism connected to the constant force spring. The engagement mechanism first fires the stylet, initiates concurrent cannula firing, and then completes cannula firing. The biopsy device provides a time delay to allow tissue to more effectively prolapse into the stylet tissue sample recess.

A safety cover is also provided to prevent accidental firing of the biopsy instrument.

BRIEF DESVRIPTION OF THE DRAWINGS

FIG. 5 is an enlarged, cross-sectional view of an interlocking mechanism.

DETAILED DESCRIPTION OF THE INVENTION

Although the present invention can be made in many different forms, the preferred embodiments are described in this disclosure and shown in the attached drawings. This disclosure exemplifies the principles of the present invention and does not limit the broad aspects of the invention only to the illustrated embodiments.

Figure 1:
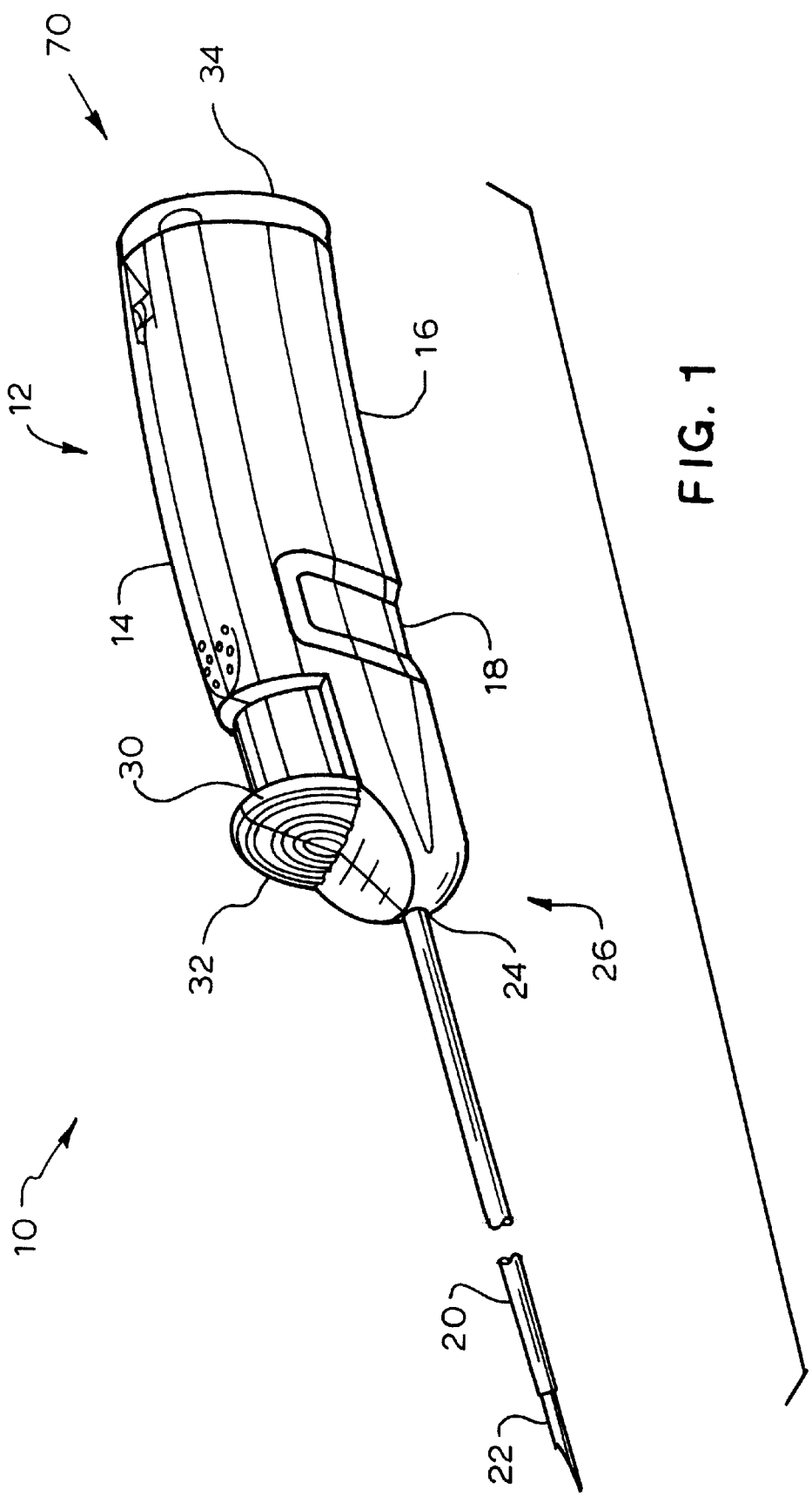
FIG. 1 is a perspective view of a biopsy instrument made in accordance with the principles of the present invention.
Figure 6:
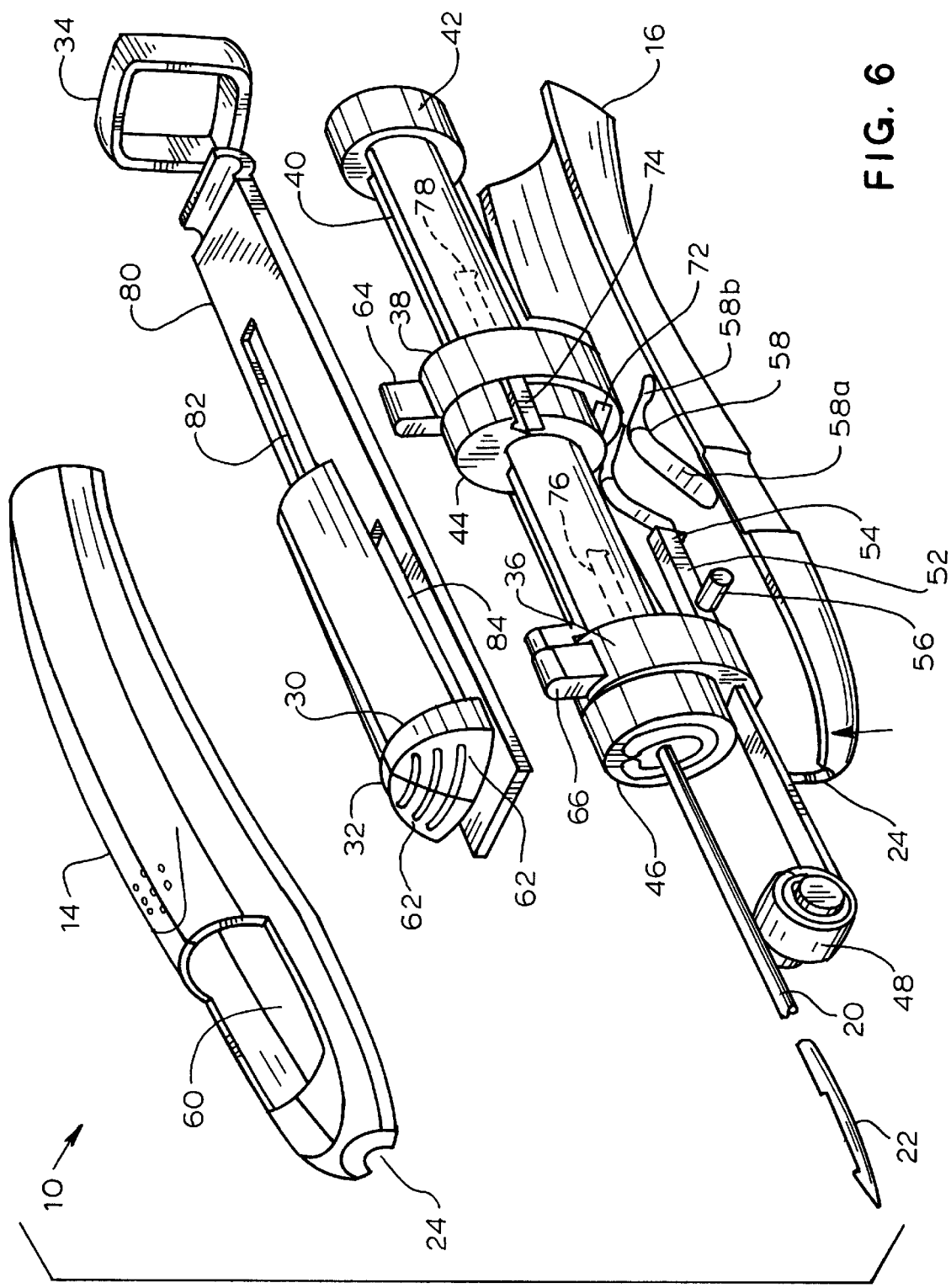
FIG. 6 is an exploded, perspective view of an alternative embodiment of a biopsy instrument made in accordance with the principles of the present invention.

FIG. 1 shows a perspective view of a biopsy instrument 10 made in accordance with the principles of the present invention. The biopsy instrument 10 includes a housing 12 having a left housing 14 and a right housing 16. The housing could be made from other components, for example, an upper housing and a lower housing as shown in FIG. 6. Referring to FIG. 1, preferably, the housing 12 is ergonomically designed to conform to the human hand and may include one or more finger rests 18. The ergonomic design includes a housing shape that coincides with contours of the human hand and is comfortable to hold. The biopsy instrument 10 also includes a cannula actuator 30, a stylet actuator 32, and a safety cover 34 as described below.

Figure 2:
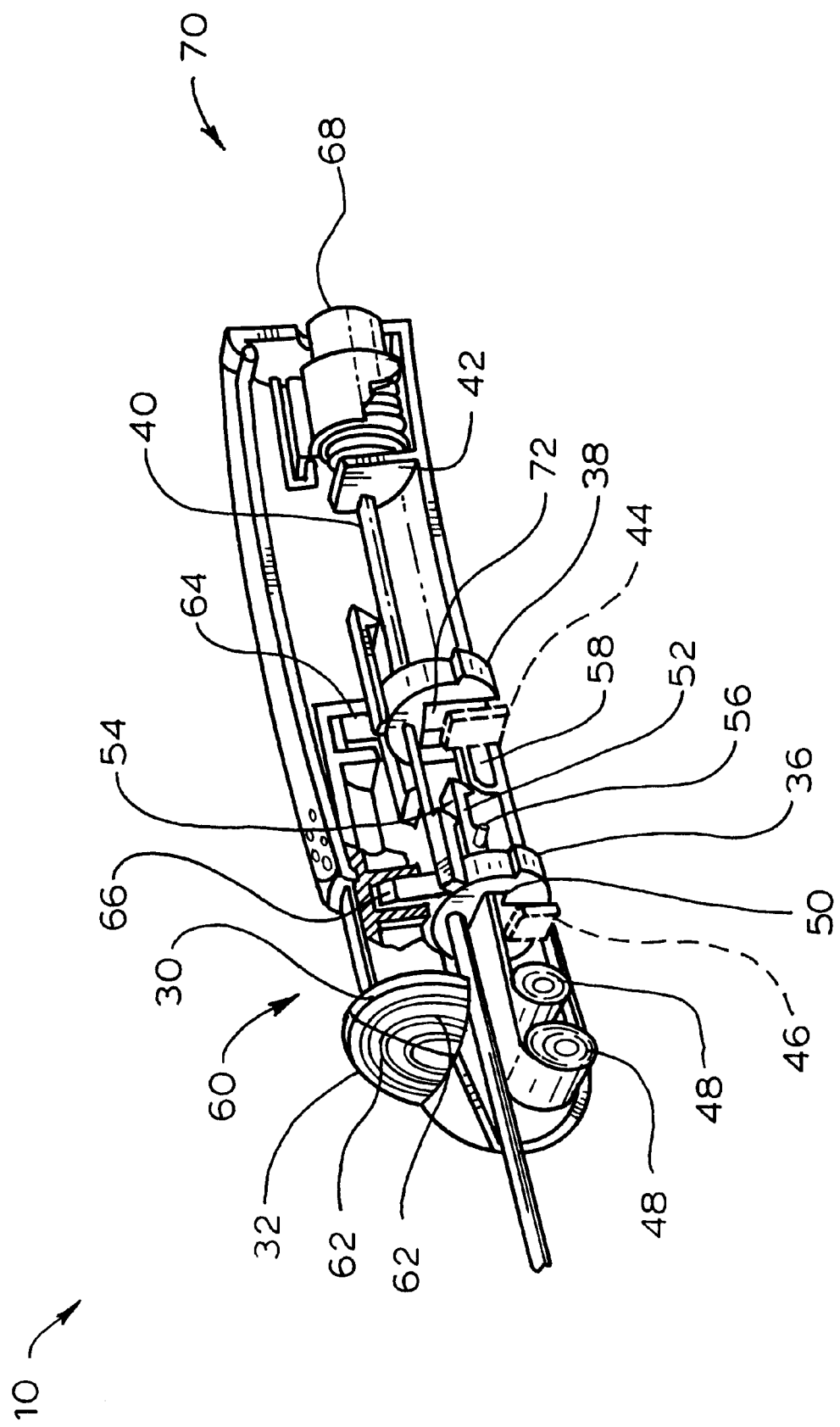
FIG. 2 is a cross-sectional, perspective view of a biopsy instrument made in accordance with the principles of the present invention.
Figure 3:
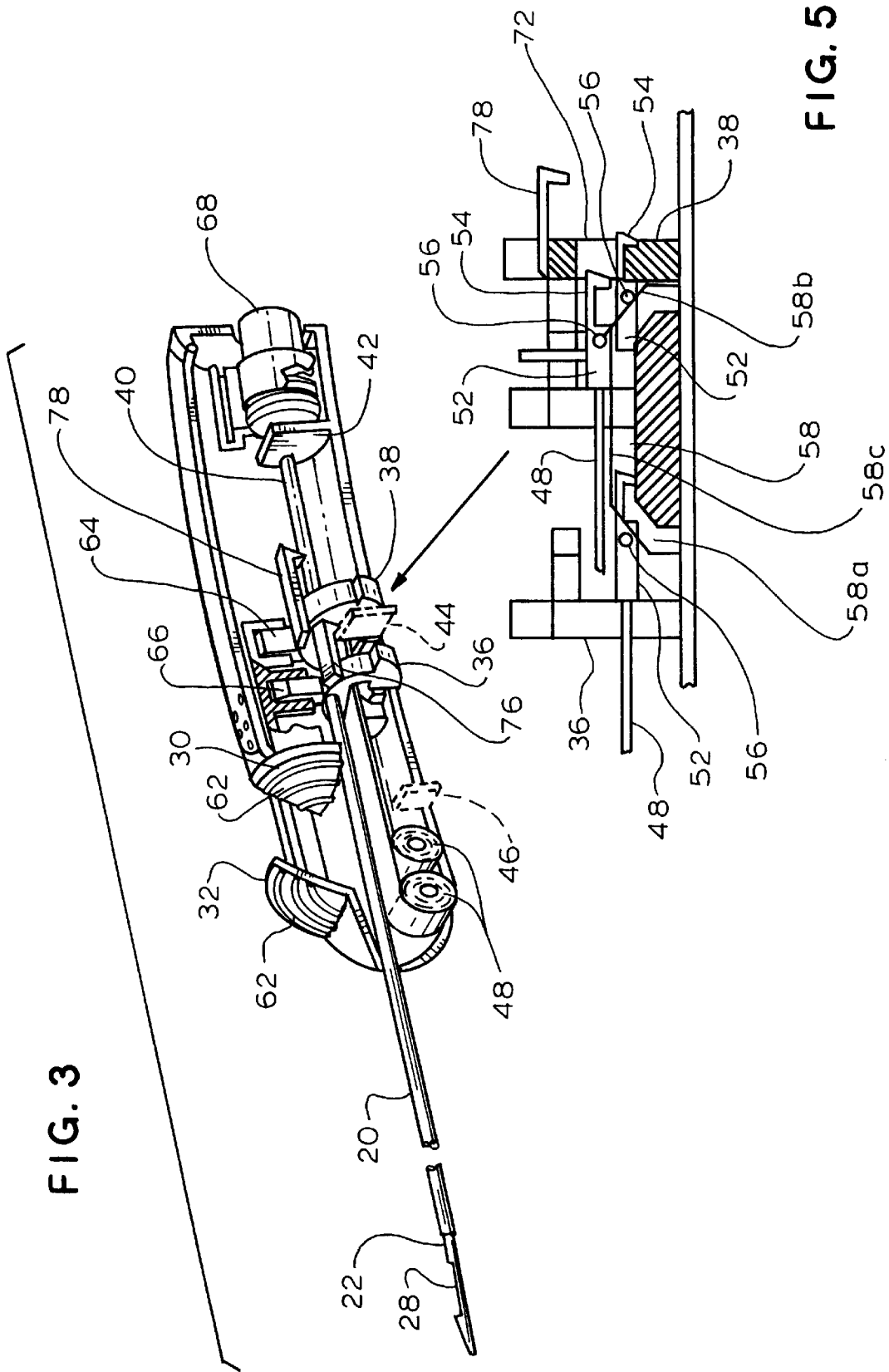
FIG. 3 is a cross-sectional view of the biopsy instrument of FIG. 2 in a cannula retracted mode.

A cannula 20 and a stylet 22 are slidably contained within the housing 12 and extend out of an opening 24 in a housing end 26. The cannula 20 is a hollow needle having a sharp, open end. The stylet 22 is a solid needle having a pointed end and a tissue sample recess 28. The recess 28 is shown in FIG. 3. The stylet 22 is slidably positioned within the cannula 20 and extends beyond the cannula end, FIG. 2 shows a cross-sectional, perspective view of a biopsy instrument 10 made in accordance with the principles of the present invention. The cannula 20 and the stylet 22 are permanently attached to two self-guided slides, a cannula slide 36 and a stylet slide 38, respectively. The cannula and stylet slides 36, 38 are axially slidable on a guide 40 connected to the housing 12. There may be two guides 40, one guide 40 on each half of the housing. The stylet slide 38 is slidable between a rear stop block 42 and a middle stop block 44, and the cannula slide 36 is slidable between the middle stop block 44 and a front stop block 46. The front, middle, and rear stop blocks 42, 44, 46 are permanently secured to the housing 12 at their respective locations.

Accordingly, the stylet slide 38 is slidable between a first position adjacent the rear stop block 42 and a second position adjacent the middle stop block 44. The cannula slide 36 is slidable between a first position adjacent the middle stop block 44 and a second position adjacent the front stop block 46. When the stylet slide 38 and the cannula slide 36 are in their first positions, a portion of the stylet 22 and a portion of the cannula 20 are retracted into the instrument 10. When the stylet slide 38 and the cannula slide 36 are in their second positions, the stylet 22 and cannula 20 are advanced out of the instrument 10.

A constant force spring 48 provides the driving force for the stylet 22 and the cannula 20. The constant force spring 48 maintains a constant speed of travel for both the stylet 22 and the cannula 20. The constant force spring 48 is a rotatable and flexible spring coil. Also one or more constant force springs 48 can be utilized by connecting the multiple springs at their non-coiled ends. Accordingly, multiple springs 48 having relatively small coil diameters can be utilized to supply the same force as a single spring 48 having a relatively larger coil diameter. The Coiled end of the spring. 48 is secured to the housing 12 and the free end of the-spring 48 slidably extends through a passageway 50 in the cannula slide 36 and is attached to an engagement mechanism 52.

The engagement mechanism 52 includes an interlock end 54 and a cam surface 56. The cam surface 56 of the engagement mechanism 52 cams along a ramp 58 to alternatively interlock and release the interlock end 54 with the stylet slide 38 as described in detail below. The engagement mechanism 52 may include multiple cam surfaces 56 that cam along multiple spaced apart ramps 58, as shown more clearly in FIG. 6, for example.

Referring to FIG. 2, the cannula actuator 30 and the stylet actuator 32 are independent and slidably extend along the housing 12 and through a housing opening 60. The stylet actuator 32 and the cannula actuator are juxtaposed. Particularly, the cannula actuator 30 and the stylet actuator 32 are positioned side-by-side each other to permit actuation of both actuators 30, 32 by a single finger of a single hand without repositioning the hand. The actuators 30, 32 provide a mechanism to place the biopsy device 10 in a ready mode as described in detail below. The actuators 30, 32 include a finger surface 62 which can be contacted by a single finger of a single human hand to actuate (slide) the actuators 30, 32. A projection 64 on the stylet slide 38 engages the stylet actuator 32. Likewise, a projection 66 on the cannula slide 36 engages the cannula actuator 30.

A spring loaded firing trigger 68 is provided at a distal end 70 of the instrument 10 opposite of the proximal front end 26. The firing trigger 68 is pressed to fire the instrument 10. Particularly, the firing trigger 68 fires and releases the stylet 22 as described below. The hinged safety cover 34 (shown in FIG. 1) is provided to prevent accidental firing of the instrument. The safety cover 34 can be moved between a first position covering the firing trigger 68 and a second position allowing access to the firing trigger 68. The firing trigger 68 could be placed at any location on the instrument 10, including the proximal front end, and an appropriate mechanism provided to fire the instrument 10.

Operation of the biopsy instrument 10 will be described with reference to FIGS. 2–5. Initially, FIG. 2 shows the instrument 10 in a fired mode. The biopsy instrument 10 is placed in a ready mode by holding the instrument 10 in a single hand in a first position and actuating the cannula actuator 30 and the stylet actuator 32 to retract the cannula 20 and the stylet 22.

Referring to FIG. 3, a cross-sectional view of the biopsy instrument 10 in a cannula retracted mode is shown. First, the cannula actuator 30 is retracted rearwardly by a finger of the same single hand contacting the finger surface 62. The cannula actuator 30 engages the projection 66 on the cannula slide 36 and slides the cannula slide 36 and the cannula 20 rearwardly against the force of the constant force spring 48.

The engagement mechanism 52 is abutted against the cannula slide 36 and thus, the spring 48 is uncoiled as the cannula actuator 30 is actuated.

FIG. 5 shows an enlarged, cross-sectional view of an interlocking mechanism in three stages. The first stage is shown where the cannula slide 36 retracts, the cam surface 56 of the engagement mechanism 52 is advanced and elevated along a first cam surface 58a of the ramp 58. The second stage is when the cam surface 56 slides along a horizontal ramp surface 58c. The interlock end 54 of the engagement mechanism 52 is guided into a lock 72 on the stylet slide. The third stage is shown as the engagement mechanism cam surface 56 advances and descends along a second cam surface 58b of the ramp 58; the interlock end 54 releasably locks to the lock 72 of the stylet slide 38.

Figure 4:
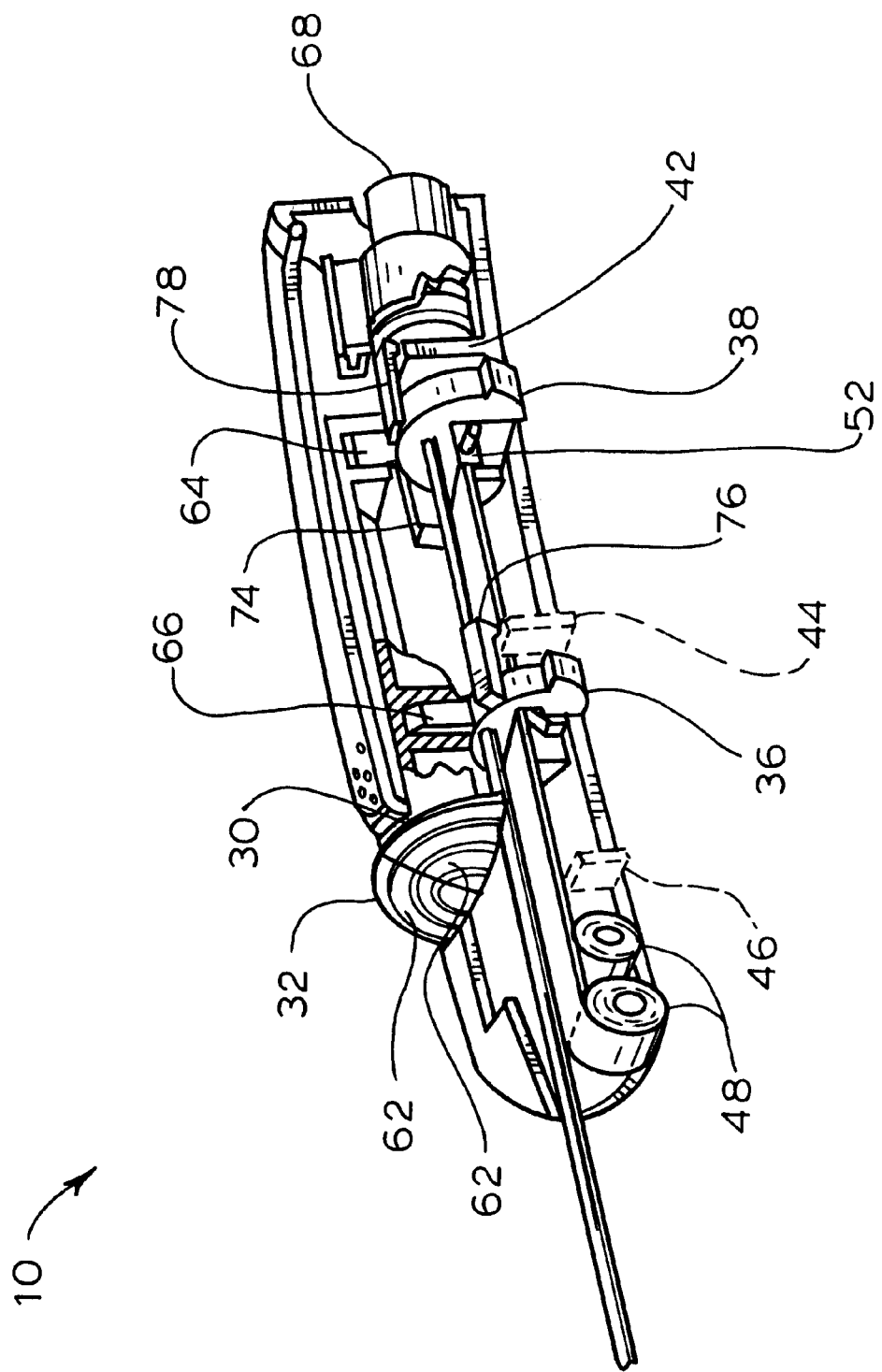
FIG. 4 is a cross-sectional view of the biopsy instrument of FIG. 2 in a cannula and stylet retracted mode.

Referring to FIG. 3, the cannula slide 36 contacts a first stylet latch 74 and releases the stylet slide 38 from being latched to the middle stop block 44. The first stylet latch 74 is shown in FIG. 4 unlatched to the middle stop block 44. As shown in FIG. 3, a cannula latch 76 latches the cannula slide 36 to the middle stop block 44. In this position of the instrument 10, the cannula 20 is retracted and the stylet tissue sample recess 28 is exposed. If a tissue sample had previously been captured within the recess 28, the tissue sample could now be expelled.

Referring to FIG. 4, a cross-sectional view of the biopsy instrument 10 in a cannula and stylet retracted mode (instrument ready for firing mode) is shown. Second, while the same single hand remains in its first position on the instrument 10, the stylet actuator 32 is retracted rearwardly by the same finger contacting the finger surface 62 on the stylet actuator 32. The stylet actuator 32 engages the projection 64 on the stylet slide 38 and slides the stylet slide 38 and the stylet 22 rearwardly against the force of the constant force spring 48. The engagement mechanism 52 is locked to the stylet slide 38 and thus, the spring 48 is further uncoiled as the stylet actuator 32 is actuated. A second stylet latch 78 latches the stylet slide 38 to the rear stop block 42. In this position of the instrument 10, both the cannula 20 and the stylet 22 are retracted and the biopsy instrument 10 is ready for firing.

In the ready mode, the stylet 22 and the cannula 20 are inserted into a patient in the area where a tissue sample is desired.

The biopsy instrument 10 is fired by moving the safety cover 34 at the rear end 70 of the housing 12 away from the spring loaded trigger 68 and depressing the trigger 68. The trigger 68 releases the second stylet latch 78 and the spring 48 propels the stylet slide 38 and the stylet 22 forward extending the stylet 22 into the tissue. The stylet recess 28 is exposed and the tissue prolapses into the recess 28. The stylet slide 38 advances forward until it contacts the middle stop block 44, and at that point the first stylet latch 74 latches onto the middle stop block 44. The first stylet latch 74 latches onto the middle stop block 44 to prevent the stylet 22 from recoiling as the cannula 20 advances forward.

As the stylet slide 38 approaches the middle stop block 44, the stylet slide 38 impacts the cannula latch 76 and moves the cannula latch 76 radially outward and axially forward. The forward axial movement of the cannula latch 76 initiates forward movement of the cannula slide 36 and the cannula 20 simultaneously and concurrently with the forward travel of the stylet 22.

As the stylet slide 38 approaches the middle stop block 44, the cam surface 56 of the engagement mechanism 52 is elevated along the ramp second cam surface 58b. After the cannula 20 has started its forward motion, the interlock end 54 is elevated sufficiently to be released from the stylet slide lock 72.

The engagement mechanism 52 continues to travel forwardly under the force of the spring 48 and abuts the cannula slide 36. The constant force spring 48 advances the cannula slide 36 and the cannula 22 until the cannula slide 36 contacts the front stop block 46. After the concurrent stylet 22 and cannula 20 motion, the cannula 20 briefly stops until the spring 48 resumes movement of the cannula 20. For example, there may be approximately a millisecond time delay. The time delay provided by the engagement mechanism 52 and the ramp 58 allows additional time for the tissue to prolapse into the stylet recess 28.

As the cannula 20 advances over the stylet 22, the cannula 20 severs the tissue and captures a tissue sample within the recess. After the tissue sample is captured, the biopsy instrument 10 is removed from the patient. The cannula 20 can be retracted as discussed above to expose the tissue sample and remove the sample from the biopsy instrument 10.

The biopsy instrument 10 only permits a specific actuation sequence of the cannula 20 and the stylet 22. The cannula 20 must be retracted prior to retraction of the stylet 22 because in the fired mode, the stylet slide 38 is latched to the middle stop block 44. The stylet slide 38 is unlatched from the middle stop block 44 only by the cannula slide 36 contacting the first stylet latch 74. This prevents a captured tissue sample from being dragged along the inside of the cannula 20 and damaged. In other words, the cannula actuator 30 is actuated independently of the stylet actuator 32, and subsequently the stylet actuator 32 is actuated. The cannula actuator 30 and the stylet actuator 32 return to their forward positions as shown in FIG. 1 as the stylet 22 and the cannula 20 are fired.

FIG. 6 shows an exploded, perspective view of an alternative embodiment of a biopsy instrument 10 made in accordance with the principles of the present invention. Components of the alternative biopsy instrument 10 shown in FIG. 6 are identified by the same reference numerals as used in FIGS. 1–5.

The biopsy instrument 10 shown in FIG. 6 includes an upper housing 14 and a lower housing 16. A guide 40 is a separate component from the housing. The stylet slide 38 and the cannula slide 36 slide along the guide 40. The front stop block 46, the middle stop block 44, and the rear stop block 42 are attached to the guide 40 in their respective locations. The cannula actuator 30 and the stylet actuator 32 slide on an actuator support 80. The actuator support 80 includes two slots 82, 84. The projection 64 on the stylet slide 38 extends through and slides along the slot 82 such that the stylet actuator 32 engages the stylet slide 38. Likewise, the projection 66 on the cannula slide 36 extends through and slides along the slot 84 such that the cannula actuator 30 engages the cannula slide 36.

Figure 7:
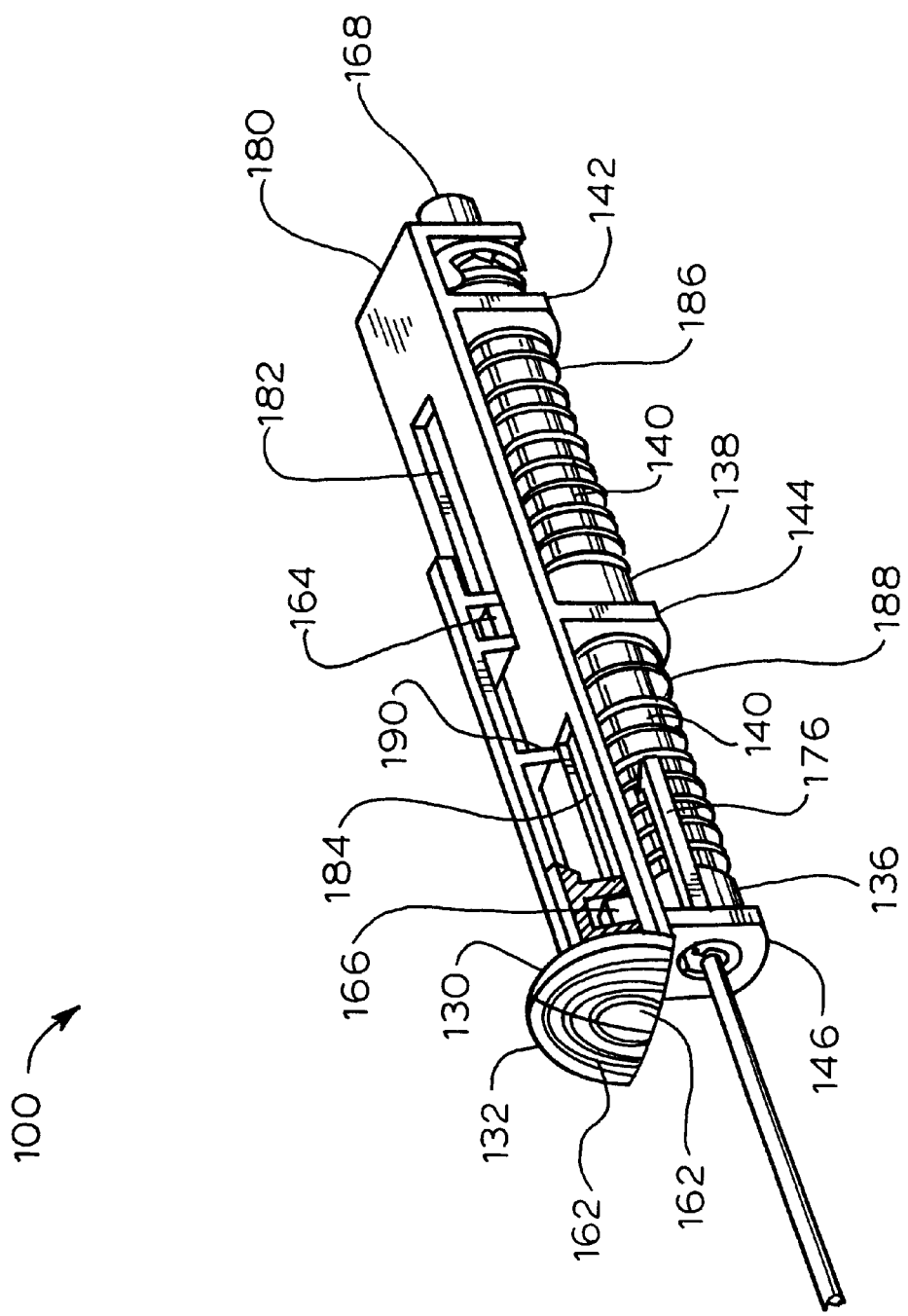
FIG. 7 is a perspective view of another alternative embodiment of a biopsy instrument made in accordance with the principles of the present invention.

FIG. 7 shows a perspective view of the internal components of an alternative embodiment of a biopsy instrument 100 made in accordance with the principles of the present invention. Components of the alternative biopsy instrument 100 which are similar to the components in biopsy instrument 10 of FIG. 2 are identified by corresponding numerals in the 100 series.

The biopsy instrument 100 includes two springs, a stylet spring 186 and a cannula spring 188. The stylet spring 186 is positioned between the rear stop block 142 and the stylet slide 138, and biases the stylet slide 138 forward. Likewise, the cannula spring 188 is positioned between the middle stop block 144 and the cannula slide 136, and biases the cannula slide 136 forward. In the fired mode, as shown in FIG. 7, the springs 186, 188 constantly exert forward biasing forces on the slides 138, 136. Accordingly, the first stylet latch on the stylet slide 138 has been removed because the stylet spring 186 prevents the stylet 122 from recoiling when the cannula 120 is fired.

Figure 8:
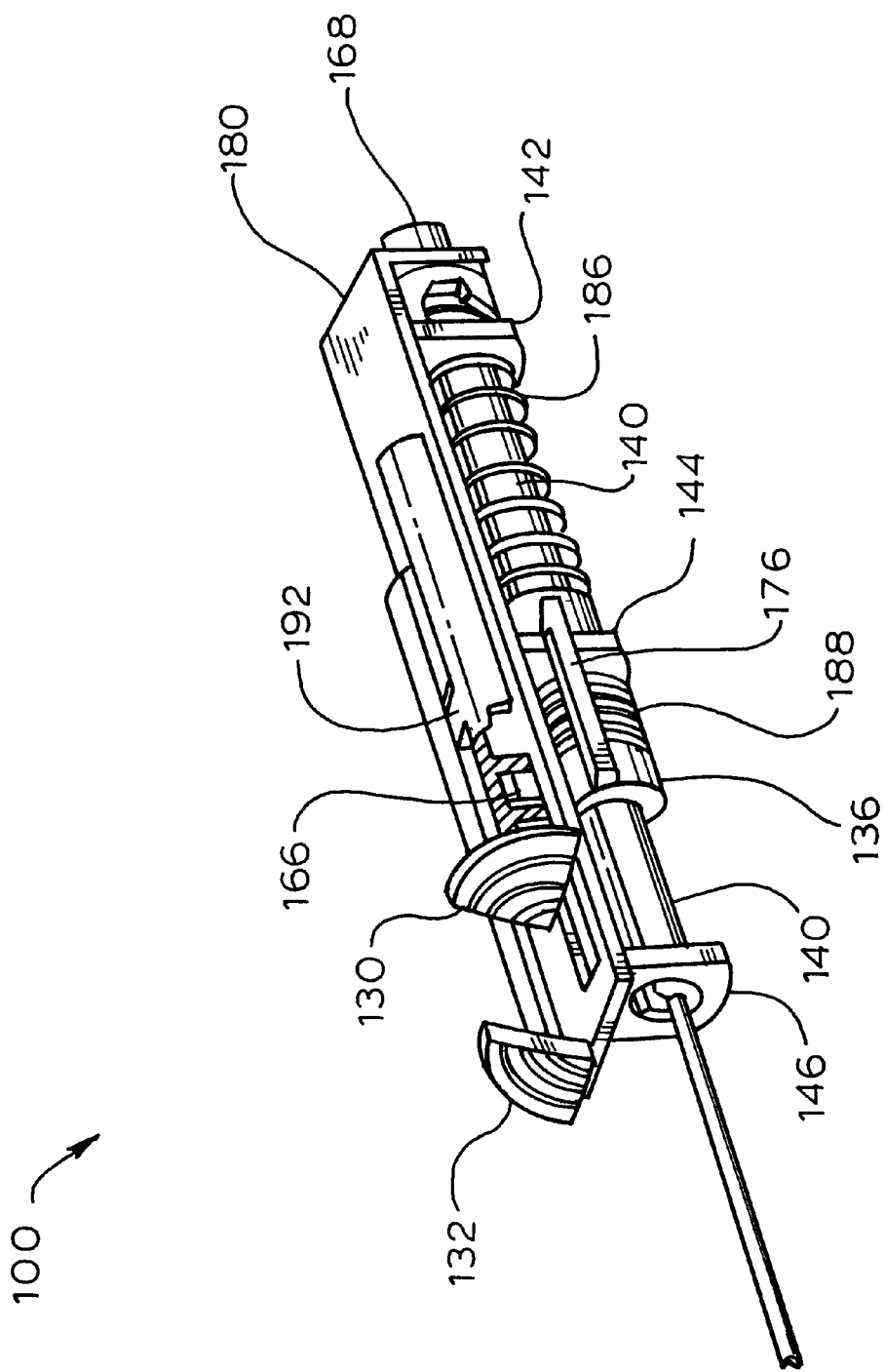
FIG. 8 is a perspective view of the biopsy instrument of FIG. 7 in a cannula retracted mode.
Figure 9:
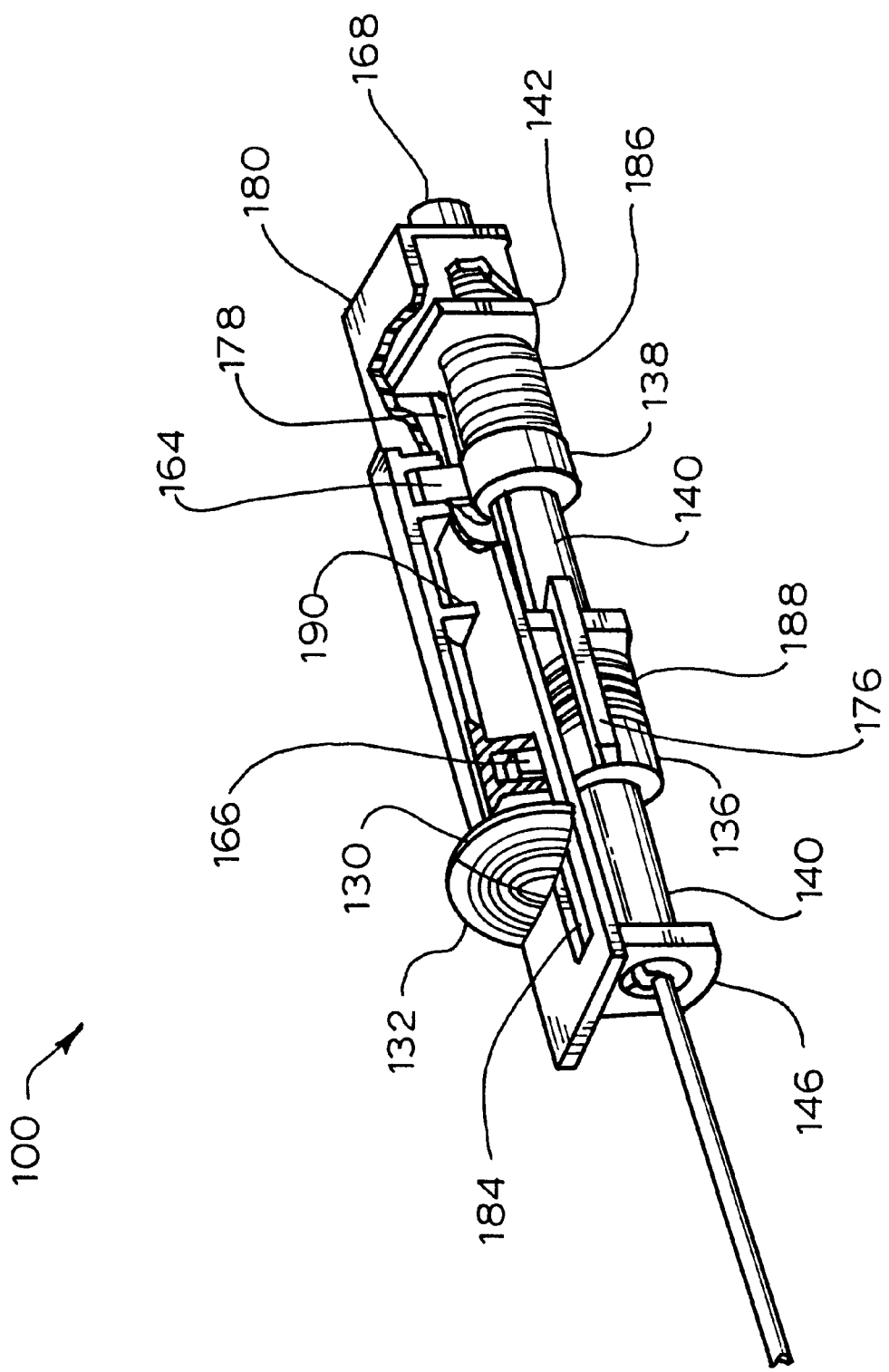
FIG. 9 is a perspective, partial cross-sectional view of the biopsy instrument of FIG. 7 in a cannula and stylet retracted mode.

The biopsy instrument 100 can be placed in a ready mode by actuating the cannula actuator 130 and the stylet actuator 132 in three different sequences. Referring to FIGS. 7–9, the first actuating or cocking sequence is the same as described above with reference to the instrument 10 shown in FIGS. 2–4 in which the cannula actuator 130 is actuated first and independently of the stylet actuator 132, and subsequently the stylet actuator 132 is actuated.

Referring to FIG. 9, the second actuating sequence is simultaneous actuation of the cannula actuator 130 and the stylet actuator 132 by a single finger while the finger contacts both actuators 130, 132 simultaneously. The single finger of the single hand is simultaneously placed on both of the finger surfaces 162. The side-by-side location of the actuators 130, 132 allows for the single finger to contact both of the finger surfaces 162. As the single finger actuates both actuators 130, 132, the stylet 122 and cannula 120 are retracted simultaneously.

The third actuating sequence also simultaneously actuates the cannula actuator 130 and the stylet actuator 132. The third sequence includes a single finger contacting only the finger surface 162 of the stylet actuator 132. Referring to FIGS. 7 and 9, as the stylet actuator 132 is actuated, a wall 190 on the stylet actuator 132 engages a projection 192 on the cannula actuator 130. The projection 192 is shown in FIG. 8. Accordingly, as the stylet actuator 132 slides rearwardly, the cannula actuator 130 simultaneously slides rearwardly.

Regardless of which actuation sequence is utilized for the instrument shown in FIGS. 7–9, the stylet 122 cannot be retracted prior to retraction of the cannula 120. This prevents a captured tissue sample from being dragged along the inside of the cannula 120 and damaged. The three actuating sequences provide medical personnel with flexibility in placing the biopsy instrument 100 in a ready mode, while, preventing retraction of the stylet 122 prior to retraction of the cannula 120.

While the preferred embodiments have been illustrated and described, numerous changes and modifications can be made without significantly departing from the spirit and scope of this invention. Therefore, the inventors intend that such changes and modifications be covered by the appended claims.

What is claimed is:

1. A biopsy device comprising:
    a housing;
    a cannula slidably extending from the housing through an opening;
    a stylet slidably positioned within the cannula;
    a stylet actuator associated with the stylet to retract the stylet within the housing; and,
    a cannula actuator associated with the cannula to retract the cannula within the housing, the cannula actuator juxtaposed the stylet actuators;
    wherein the stylet actuator and the cannula actuator are actuable in three sequences:
        a first sequence wherein the cannula actuator is actuated independently of the stylet actuator and subsequently the stylet actuator is actuated;
        a second sequence wherein the cannula actuator and the stylet actuator are actuated simultaneously; and,
        a third sequence wherein the stylet actuator is actuated and engages the cannula actuator such that the cannula actuator is actuated simultaneously with the stylet actuator.

2. The biopsy device of claim 1 further comprising means contained within the housing for biasing the stylet and the cannula toward a first end of the housing.

3. The biopsy device of claim 2 wherein the means for biasing comprises a first means for biasing the stylet and a second means for biasing the cannula.

4. The biopsy device of claim 3 wherein the first means for biasing is a first spring, and the second means for biasing is a second spring.

5. The biopsy device of claim 1 further comprising:
    a cannula slide attached to the cannula, the cannula actuator engagable with the cannula slide to retract the cannula; and,
    a stylet slide attached to the stylet, the stylet actuator engagable with the stylet slide to retract the stylet.

6. The biopsy device of claim 5 wherein the stylet actuator engages the cannula actuator when the stylet actuator is actuated.

7. A biopsy device comprising:
    a stylet slidably positioned within a cannula;
    a stylet actuator associated with the stylet to move the stylet from_a first stylet position to a second stylet position when the stylet actuator is actuated; and,
    a cannula actuator associated with the cannula to move the cannula from a first cannula position to a second cannula position when the cannula actuator is actuated;
    wherein the stylet actuator and the cannula actuator are actuatable in three sequences:
        a first sequence wherein the cannula actuator is actuated independently of the stylet actuator and subsequently the stylet actuator is actuated;
        a second sequence wherein the cannula actuator and the stylet actuator are actuated simultaneously; and,
        a third sequence wherein the stylet actuator is actuated and engages the cannula actuator such that the cannula actuator is actuated simultaneously with the stylet actuator.

* * * * *